United States Patent [19]

Osborn, III et al.

[11] Patent Number: 5,817,047
[45] Date of Patent: Oct. 6, 1998

[54] TAMPON AND METHOD OF MAKING SAME

[75] Inventors: Thomas Ward Osborn, III, Cincinnati; Edward John Milbrada, West Chester, both of Ohio

[73] Assignee: The Procter & Gamble Company, Cincinnati, Ohio

[21] Appl. No.: 818,919

[22] Filed: Mar. 17, 1997

[51] Int. Cl.$^6$ .................................................. A61F 13/20
[52] U.S. Cl. ............................ 604/14; 604/15; 604/904; 604/363
[58] Field of Search .................................. 604/363, 904, 604/11–18

[56] References Cited

U.S. PATENT DOCUMENTS

| | | |
|---|---|---|
| 3,760,808 | 9/1973 | Bleuer ........................................ 604/14 |
| 3,902,493 | 9/1975 | Baier et al. . |
| 4,077,409 | 3/1978 | Murray et al. .......................... 128/285 |
| 4,186,742 | 2/1980 | Donald . |
| 4,286,596 | 9/1981 | Rubinstein . |
| 4,405,323 | 9/1983 | Auerbach . |
| 4,413,986 | 11/1983 | Jacobs . |
| 4,424,054 | 1/1984 | Conn et al. . |
| 4,431,427 | 2/1984 | Lefren et al. . |
| 4,447,222 | 5/1984 | Sartinoranont . |
| 4,486,191 | 12/1984 | Jacob . |
| 4,563,485 | 1/1986 | Fox, Jr. et al. . |
| 4,585,792 | 4/1986 | Jacob et al. . |
| 4,620,534 | 11/1986 | Zartman . |
| 4,637,820 | 1/1987 | Marini et al. . |
| 4,661,101 | 4/1987 | Sustmann . |
| 4,722,936 | 2/1988 | Jacob ..................................... 514/474 |
| 4,722,937 | 2/1988 | Jacob et al. . |
| 4,769,021 | 9/1988 | Kass . |
| 4,795,422 | 1/1989 | Conner et al. . |
| 4,923,440 | 5/1990 | Genaro . |
| 4,952,211 | 8/1990 | Snider . |
| 5,000,749 | 3/1991 | LeVeen et al. . |
| 5,070,889 | 12/1991 | Leveen et al. . |
| 5,389,374 | 2/1995 | Brown-Skrobot . |

FOREIGN PATENT DOCUMENTS 0 720 821 A2  10/1996  European Pat. Off. .

OTHER PUBLICATIONS

Wagner, et al., "Tampon–induced changes in vaginal oxygen and carbon dioxide tensions," *Am. J. Obstet. Gynecol.*, vol. 148, No. 2, pp. 147–150 (Jan. 15, 1984).

Schlievert, "TSST–1: Structure, Function, Purification, and Detection," *Reviews of Infectious Diseases*, vol. 11, Suppl. 1, pp. S107–S109 (Jan.–Feb. 1989).

Broome, "Epidemiology of Toxic Shock Syndrome in the United States: Overview," *Reviews of Infectious Diseases*, vol. 11, Suppl. 1, pp. S14–S21 (Jan.–Feb. 1989).

Lee, et al., "Investigation by Syringe Method of Effect of Tampons on Production In Vitro of Toxic Shock Syndrome Toxin 1 by *Staphylococcus aureus*," *Journal of Clinical Microbiology*, vol. 25, No. 1, pp. 87–90 (Jan. 1987).

Robbins, et al., "Production of Toxic Shock Syndrome Toxin 1 by *Staphylococcus aureus* as Determined by Tampon Disk–Membrane–Agar Method," *Journal of Clinical Microbiology*, vol. 25, No. 8, pp. 1446–1449 (Aug. 1987).

*Primary Examiner*—John G. Weiss
*Assistant Examiner*—Dennis Ruhl
*Attorney, Agent, or Firm*—Marshall, O'Toole, Gerstein, Murray & Borun

[57] ABSTRACT

Absorptive pads including catamenial tampons are provided which are characterized by $O_2$ levels sufficiently reduced so as to reduce the introduction of air into the vaginal canal with a resulting reduction in the probability of production of toxic shock syndrome exotoxin during internal use of the pads.

26 Claims, 3 Drawing Sheets

TAMPON AND METHOD OF MAKING SAME

BACKGROUND OF THE INVENTION

The invention relates generally to absorptive pads for internal use including surgical and wound dressings and packings, and surgical sponges and more specifically to catamenial tampons. The invention further relates to such absorptive pads intended to reduce the introduction of air into the vaginal canal with a resulting reduction in the probability of production of toxic shock syndrome exotoxin as a result of insertion of such pads and methods for production of such pads.

Toxic shock syndrome is a syndrome with a high mortality rate characterized by rapid onset of high fever, vomiting, diarrhea and rash followed by a rapid drop in blood pressure and vital organ failure. Toxic shock syndrome is associated with the presence of *Staphylococcus aureus* bacteria and one or more exotoxins which are produced by the bacteria. The exotoxins associated with toxic shock syndrome include Exotoxin A, B, and C, Pyrogenic Exotoxin C, Enterotoxin A, Enterotoxin B, Enterotoxin C, Staphylococcal Enterotoxin F and Toxic Shock Syndrome toxin-1. Toxic shock syndrome is not caused by the bacteria per se but rather by the toxic effects of the associated exotoxin which can pass from the vagina and other internal body cavities into the bloodstream.

Toxic shock syndrome has been found to be associated with the use of absorptive pads within the vagina which may promote the growth of bacteria and the production of exotoxin in their vicinity. The syndrome has been observed with surgical dressings but appears to be particularly associated with the use of catamenial tampons. The syndrome appears to occur with elevated frequency in association with those absorptive pads which are characterized by high levels of absorbency and which accordingly are left inside the body for extended periods. Of interest to the present invention is the observation of Robbins et al., *J. Clin. Microbiol.*, 25, 1446–1449 (1987) that the main role of tampons in toxic shock syndrome may be that of providing a fibrous surface for heavy colonization and sufficient air for toxin production. Lee et al., *J. Clin. Microbiol.*, 25, 87–90 (1987) suggest that elevated levels of $CO_2$ promote toxin production.

While a preferred approach for reducing the risk of toxic shock syndrome when using absorptive pads is to frequently exchange new pads for used ones, various other approaches have been proposed by the art for reducing the risk of toxic shock syndrome associated with an internal absorbent pad. One approach is the incorporation of antibiotics or other bactericides into the absorbent pad such as described in Leveen et al., U.S. Pat. No. 5,000,749 and U.S. Pat. No. 5,070,889 which describe use of iodine bactericides in tampons and catamenial sponges. Such an approach is not always suitable for use in a catamenial product, however, because a bactericide which is active against *Staphylococcus aureus* can adversely affect other beneficial bacteria which make up the vaginal flora. In a related method, Lefren et al., U.S. Pat. No. 4,431,427 describes the use of catamenial tampons comprising substances such as organic acids which will maintain a pH of about 4.5 to 2.5 in the fluids absorbed during use of the tampons such that the growth of pathogenic bacteria is inhibited.

Other approaches are directed to inactivation of the toxic shock syndrome exotoxin. Jacob et al., U.S. Pat. No. 4,585,792; U.S. Pat. No. 4,722,936; and U.S. Pat. No. 4,722,937 describe the administration of L-ascorbic acid for the detoxification of the *Staphylococcus aureus* toxins Pyrogenic Exotoxin C and Staphylococcal Enterotoxin F. While Jacob et al. do not ascribe a mechanism for the effectiveness of ascorbic acid at neutralizing toxic shock syndrome exotoxin they observe that L-ascorbic acid is known to be a reducing agent and strong anti-oxidant and that it might operate to inactivate bacterial toxins by reducing disulfide bonds within the toxins.

Another approach is directed to the incorporation of substances within an absorbent pad which inhibit the production of toxic shock syndrome exotoxins by *Staphylococcus aureus*. Kass, U.S. Pat. No. 4,769,021 describes the incorporation of non-toxic divalent magnesium cations in absorptive pads in order to reduce the concentrations of available magnesium ions below those critical for optimal production of toxic shock syndrome toxin-1 and other staphylococcus products.

Of interest to the present invention are conventional tampons and inserters of various designs including those disclosed by U.S. Pat. No. 3,902,493 to Baier, et al.; U.S. Pat. No. 4,077,409 to Murray, et al.; U.S. Pat. No. 4,286,596 to Rubinstein; U.S. Pat. No. 4,413,986 to Jacobs; U.S. Pat. Number 4,431,427 to Lefren et al.; U.S. Pat. No. 4,447,222 to Sartinoranont; and U.S. Pat. No. 4,486,191 to Jacob.

Despite these developments there remains a desire in the art for absorbent pads suitable for internal use, including catamenial tampons, which are characterized by reduced risk of toxic shock syndrome.

SUMMARY OF THE INVENTION

The present invention provides improved catamenial tampons, wherein the tampons are intended to inhibit the increased production of toxic shock syndrome exotoxin during their use. Also provided are methods for production of such tampons.

The present invention relates to the observation that while toxic shock syndrome exotoxin is produced at low levels under the anaerobic conditions which normally exist in the vagina, its production is greatly increased under aerobic conditions (i.e., in the presence of molecular oxygen, $O_2$). It has further been observed that the presence of carbon dioxide ($CO_2$) promotes the production of toxic shock syndrome exotoxin. Because absorbent pads including catamenial tampons contain in their interstices large amounts of air including $O_2$ and $CO_2$, the use of those pads in normally anaerobic environments such as the vagina can promote the production of toxic shock syndrome exotoxin.

The present invention provides a combination catamenial tampon and inserter characterized by having an $O_2$ level sufficiently reduced so as to reduce the introduction of $O_2$ into the vaginal canal with a resulting reduction in the probability of production of toxic shock syndrome exotoxin during internal use of the tampon. According to preferred embodiments, the amount of $O_2$ present in the catamenial tampon should be less than $2\times10^{-4}$ moles and preferably less than $1\times10^{-5}$ moles. According to preferred embodiments, the $O_2$ partial pressure in the vagina about 90 minutes after tampon insertion is less than about 50 mm Hg.

According to one embodiment of the invention, the $O_2$ (and $CO_2$) normally present in the pad is replaced with a biocompatible gas that does not promote production of toxic shock syndrome exotoxin. Such gases include, but are not limited to, nitrogen ($N_2$), neon, argon, helium, fluorinated hydrocarbons, and other suitable biocompatible gases having a vapor pressure of greater than 1 atmosphere at 0° C. According to another embodiment, the absorptive pad is physically sealed in a manner which prevents $O_2$, and $CO_2$ infiltration into the pad. Preferably, the tampon is sealed under a positive head pressure with a biocompatible gas which does not promote production of toxic shock syndrome exotoxin such that $O_2$ and $CO_2$ will not be introduced into the vagina during insertion of the tampon.

According to another embodiment, the pad and/or inserter can also comprise $O_2$ and/or $CO_2$ scavengers. According to yet another embodiment, the $CO_2$ level in the catamenial tampon is sufficiently reduced as to be effective in reducing the production of toxic shock syndrome exotoxin. The amount of $CO_2$ present in the catamenial tampon should be less than $3.1 \times 10^{-7}$ moles and preferably less than $1.6 \times 10^{-8}$ moles.

The invention further provides methods for producing the combination tampon and inserter comprising a catamenial tampon characterized by having an $O_2$ level sufficiently reduced as to be effective in reducing the production of toxic shock syndrome exotoxin during internal use of the tampon, and an inserter enclosing the tampon and reducing contamination of the tampon with environmental $O_2$ during storage comprising the steps of (1) producing a catamenial tampon, (2) removing $O_2$ present in the tampon, and (3) sealing the tampon with the inserter enclosing the tampon. An alternative method comprises the steps of (1) producing a catamenial tampon, (2) providing an inserter, (3) placing the tampon in the inserter, (4) removing $O_2$ present in the inserter, (5) removing $O_2$ present in the tampon, and (6) sealing the tampon with the inserter enclosing the tampon. While the tampon could be sealed in the inserter under a vacuum it is preferred that the $O_2$ present in the tampon (and in the inserter) be replaced with a biocompatible gas which does not promote production of toxic shock syndrome, preferred gases including $N_2$, neon, argon, helium, and a fluorinated hydrocarbon having a vapor pressure of greater than 1 atmosphere at 0° C.

A further alternative method of producing the combination tampon and inserter comprises the steps of (1) producing a catamenial tampon under substantially $O_2$-free conditions, (2) providing an inserter, and (3) sealing the tampon with the inserter enclosing the tampon. Preferably, the tampon is produced in the presence of a biocompatible gas which does not promote the production of toxic shock syndrome, most preferably a member selected from the group consisting of $N_2$, neon, argon, helium, and fluorinated hydrocarbons having a vapor pressure of greater than 1 atmosphere at 0° C. The step of sealing the tampon with the inserter enclosing the tampon is preferably carried out in the presence of the biocompatible gas which may then be enclosed in the inserter at an elevated positive pressure.

DETAILED DESCRIPTION

The present invention is directed to improved absorptive pads or internal use including catamenial tampons, wherein the pads are intended to inhibit the increased production of toxic shock syndrome (TSS) exotoxin during their use. Also provided are methods for production of such pads. The absorptive pads of the invention are characterized by having an $O_2$ level sufficiently reduced as to be effective in reducing the production of toxic shock syndrome exotoxin during internal use of the tampon.

Figure 1:
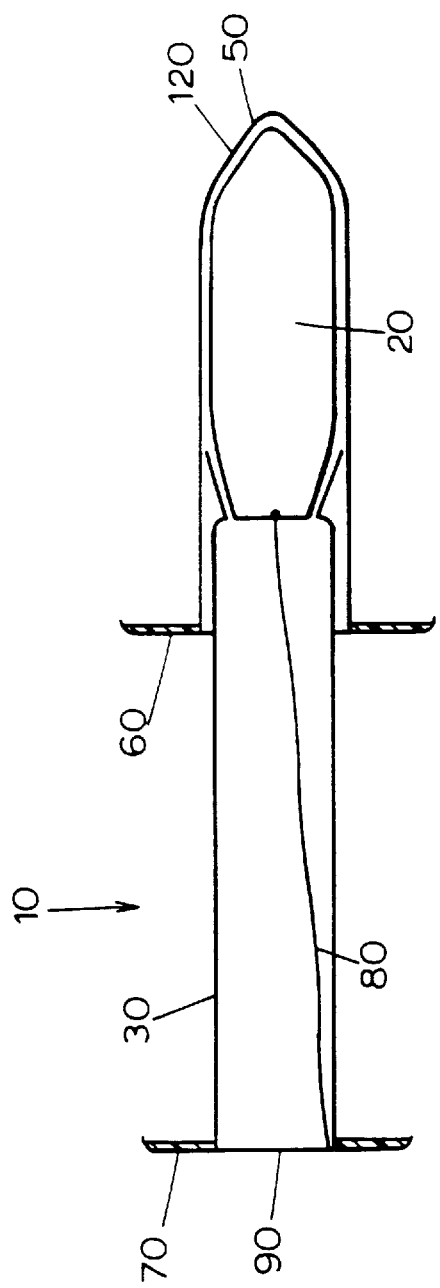
FIG. 1 is a cross-sectional side elevational view of a catamenial tampon and inserter in accordance with the present invention.

The physical features of this invention are referenced by FIG. 1. The combination tampon and inserter 10 is constructed with three different items: a tampon 20, an insertion means such as a plunger 30, and a sealed cylinder 50. The inserter comprises the plunger 30 and the sealed cylinder 50. The tampon 20 is disposed in the sealed cylinder 50 and is enclosed by the inserter.

The tampon 20 is intended to reduce the introduction of air into the vaginal canal with a resulting reduction in the probability of production of toxic shock syndrome exotoxin during internal use of such pads. A string 80 extends from the tampon 20 and preferably is retained in the rear portion of the plunger 30 to prevent the string 80 from acting as a channel for air from the surroundings to enter the plunger 30. Insertion of the tampon 20 is accomplished by pushing a gripping means 70 or the rear end of the plunger 30 towards a gripping means 60 or rear end of the sealed cylinder 50. The forward end or end of the sealed cylinder 50 distal to the plunger 30 will then rupture upon insertion to allow the tampon 20 to enter the user's vagina.

Figure 2:
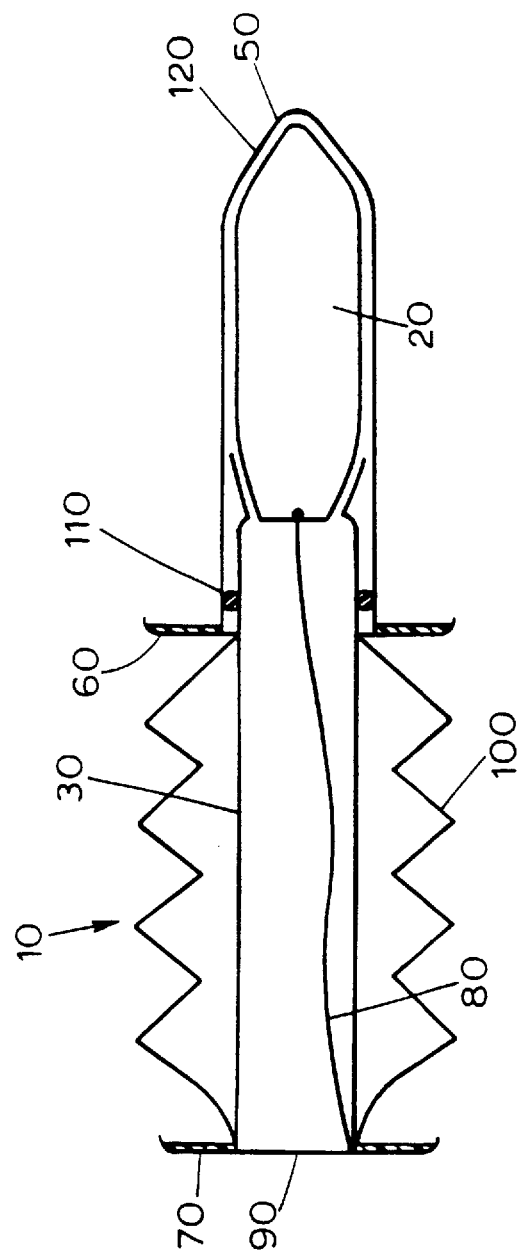
FIG. 2 is a cross-sectional side elevational view of a catamenial tampon and inserter having a bellows device in accordance with the present invention.

According to one embodiment of the invention, the inserter includes the plunger 30 at the rear end of the sealed cylinder 50. As seen in FIG. 2, the plunger 30 may include a bellows device 100 attached to or integrally sealed with the sealed cylinder 50. The bellows device 100 maintains a seal as a user presses the plunger 30 inwardly toward the sealed cylinder 50. The bellows device 100 may contain a pressurized biocompatible gas to inhibit $O_2$ and $CO_2$ from migrating from the bellows device 100 into the sealed cylinder 50. In such an embodiment, the bellows device 100 reduces the replacement of biocompatible gas by $O_2$ during storage and insertion. The bellows device 100 preferably has a permeation coefficient for nitrogen of less than about $3 \times 10^{-9}$ ($cm^3$ mm)/(sec $cm^2$ cm Hg) and a permeation coefficient for oxygen less than about $1.5 \times 10^{-9}$ ($cm^3$ mm)/(sec $cm^2$ cm Hg). (ASTM standard method D 1434-82 is suitable for measuring permeation coefficients.)

Additionally or alternatively to the bellows device 100, the inserter may include a gasket or O-ring 110 to seal the interface between the plunger 30 and the sealed cylinder 50. As an alternative to the bellows device 100, the O-ring 110 is a less bulky means for sealing the inserter. However, as mentioned above, the bellows device 100 can be filled with a pressurized biocompatible gas if desired. Preferably, a combination of the bellows device 100 and the O-ring 110 is used to seal the inserter.

Preferably, the sealed cylinder 50 is between about 5.5 and 8.5 cm in length and has an outer diameter of about 1.0 to 1.6 cm. The plunger 30 preferably has an outer diameter of about 0.6 to 1.4 cm and a length of about 6.0 to 8.1 cm. The overall length of the inserter, including the plunger 30 and the sealed cylinder 50, is preferably about 10.0 to 14 cm prior to tampon insertion. Although described above as cylindrical, the cross-sectional shape of the inserter, including the sealed cylinder 50 and the plunger 30, may be of any convenient form. It is also appropriate to make the inserter from an inexpensive plastic material. Suitable materials for forming the inserter include polymers that can be injection molded or blow molded. Alternatively, the inserter could be formed from a sufficiently stiff laminate that is rolled to form a cylinder, side seamed, with a tip being joined to one end of the cylinder. As discussed below, materials having particular permeation coefficients are preferred for inserters of some embodiments. The volume of the tampon inserter is between about 5 and 15 ml., preferably between about 6 and 12 ml.

An outwardly projecting member may be attached to the sealed cylinder 50 between the gripping means 60 and the forward end of the sealed cylinder 50. The outwardly projecting member provides a convenient means for positioning the sealed cylinder 50 by engaging the labia and preventing the forward end of the sealed cylinder 50 from being inserted too far into the vagina.

During insertion of the tampon 20 into the vagina, the plunger 30 is depressed into the sealed cylinder 50 which ruptures the end of the sealed cylinder 50 distal to the plunger 30 and introduces the tampon 20 into the user's vagina. The tampon and inserter combination 10 preferably introduces a biocompatible gas which does not promote production of toxic shock syndrome exotoxin into the vagina. The biocompatible gas further inhibits migration of $O_2$ and $CO_2$ into the vagina during removal of the inserter. Such gases include, but are not limited to, nitrogen ($N_2$), neon, argon, helium, fluorinated hydrocarbons, and other suitable biocompatible gases having a vapor pressure of greater than 1 atmosphere at 0° C.

Preferably, the $O_2$ partial pressure in the vagina 90 minutes after tampon insertion is less than about 50 mm Hg. The $O_2$ partial pressure produced in the vagina by insertion of conventional tampons using conventional inserters is disclosed by Wagner et al., *Am. J. Obstet. Gynecol.,* 148, 147–150 (1984).

The telescoping tube type inserter may have inwardly tapering flexible segments at the leading end to form a normally closed, smooth, openable, leading end. The tampon 20 is resiliently compacted and is maintained in that condition before and during insertion by placing it in the tubular inserter.

An assembly for sterile insertion into a vagina may be utilized which comprises a semirigid insertion tube, containing the tampon, telescoped inside a semirigid guide tube having a flexible sheath secured to its inner end which is tucked back into the insertion tube. The user aligns the assembly with the vaginal canal and plunges the insertion tube inward of the guide tube so that a portion of the insertion tube enters the vagina while the flexible sheath extends to sheathe the portion of the insertion tube within the vagina. Thereafter, a plunger is used to eject the tampon from the insertion tube to locate the tampon in the vagina beyond the constricting muscles. The sheath may inhibit $O_2$ and $CO_2$ from migrating into the tampon during insertion.

A flexible enclosure may be used to protect the combination tampon and inserter 10 from contamination. More particularly, the flexible enclosure seals the combination tampon and inserter 10 to prevent $O_2$ and $CO_2$ from migrating into the tampon before the tampon is inserted (i.e., during storage of the combination tampon and inserter 10).

The forward end of the tampon 20 may be flared open to a funnel configuration by the inserter during insertion. In such an inserter, a membrane is secured to the perimeter wall of the forward end of the tampon device and extends around to the forward end of the insertion cylinder where it is secured in a fused area. The membrane is used to flare the end of the tampon but also can act as a seal over the end of the tampon to inhibit $O_2$ and $CO_2$ from migrating into the tampon prior to insertion.

Conventional tampons are generally compatible with the present invention and some representative tampons are discussed below. The tampon may include cotton fibers, rayon fibers, or other materials suitable for tampons. The tampon body may be bulb-shaped. Alternatively, the tampon may have a rounder geometric shape or other tapered end to facilitate entry into the body.

The tampon may have a container on its interior for holding extra medicant. The container can release the medicants during rupture which may occur during insertion.

Additionally or alternatively, the tampon may be fully sealed to prevent atmospheric $O_2$ and $CO_2$ from migrating into the tampon.

The tampon may be compressed in a capsule prior to insertion. The bearing capsule may be prepared from a variety of non-toxic, soluble film-forming materials, such as gelatin. Foam is compressed and inserted into the capsule in the compressed state. The capsule is preferably made of a material that readily dissolves upon contact with moisture. When the capsule is inserted into the vagina, the capsule dissolves and the foam can rapidly expand to contact the vaginal periphery. The capsule may inhibit $O_2$ and $CO_2$ from migrating into the tampon.

The inserter may be covered with a gas-impervious laminate film bag or the inserter may be made out of laminated metal foil. The laminate film bag and the laminated metal foil reduce the contamination of the tampon 20 with environmental $O_2$ during storage and preferably have a permeation coefficient for nitrogen of less than about $3\times10^{-9}$ ($cm^3$ mm)/(sec $cm^2$ cm Hg) and a permeation coefficient for oxygen less than about $1.5\times10^{-9}$ ($cm^3$ mm)/(sec $cm^2$ cm Hg).

According to another embodiment of the invention, a seal 90 is located at the rear end of the plunger 30 so that the inserter can maintain a positive pressure of a biocompatible gas. The head pressure inside the tampon inserter should be greater than 1 atmosphere, preferably greater than 1.05 atmospheres, and more preferably greater than 1.1 atmospheres. The pressure inside the tampon inserter should not be too great, otherwise discomfort to the wearer may result when the seal is ruptured. Suitable gases include, but are not limited to, nitrogen preferred), neon, argon, helium, fluorinated hydrocarbons, and other biocompatible gases having a vapor pressure of greater than 1 atmosphere at 0° C. Carbon dioxide is not suitable because its presence may enhance TSS toxin production.

To maintain a positive pressure of a biocompatible gas, a seal at the forward end of the inserter may be used to ensure that the biocompatible gas does not escape into atmosphere. The tampon 20 is thus sealed in the inserter. The seal can be made by providing an end cap 120 on the inserter which is preferably integral with the cylindrical sidewalls of the inserter. The end cap 120 of the inserter may have radial lines of weakness which rupture when the plunger 30 is depressed. A tapered end cap 120 is preferred for ease of insertion.

Figure 3:
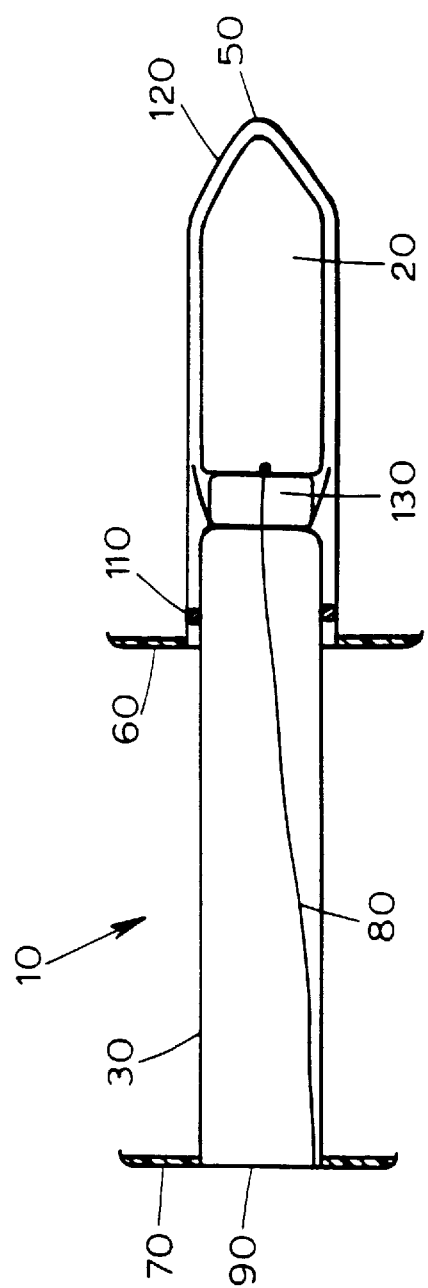
FIG. 3 is a cross-sectional side elevational view of a catamenial tampon and inserter having a gas-containing vessel.

Another embodiment, shown in FIG. 3, has a vessel 130 disposed between the tampon 20 and the plunger 30. The vessel 130 is filled with pressurized biocompatible gas such as nitrogen, argon, helium, neon, fluorinated hydrocarbons, and other suitable biocompatible gases having a vapor pressure of greater than 1 atmosphere at 0° C. During insertion, when the plunger 30 is depressed, the vessel 130 bursts as the vessel 130 is compressed between the plunger 30 and the tampon 20. The biocompatible gas released from the vessel 130 inhibits $O_2$ and $CO_2$ from migrating into the tampon 20 during insertion.

In order to maintain the requisite internal pressure and to reduce contamination of the tampon 20 with environmental $O_2$ during storage, any material used would preferably have a permeation coefficient for nitrogen of less than about $3\times10^{-9}$ ($cm^3$ mm)/(sec $cm^2$ cm Hg) and a permeation coefficient for oxygen less than about $1.5\times10^{-9}$ ($cm^3$ mm)/(sec $cm^2$ cm Hg). Materials suitable for forming the inserter include high density polyethylene, nylon 6, polyethylene terephthalate, ethylene-vinylalcohol copolymer, and polyvinylidine chloride. Nylon 6, PET, and polyvinylidine chloride are the preferred materials. Also suitable would be a laminate having a metal foil layer or the like.

According to another embodiment of the invention, an effective amount of an antioxidant (also referred to as an oxygen scavenger) can be incorporated into the inserter. The antioxidant will combine with any residual oxygen that is not removed when the inserter is filled with a biocompatible gas and sealed. Furthermore, the antioxidant will combine with any oxygen that may later diffuse into the inserter. Suitable antioxidant materials include those having a conjugated double bond such as tocopherals (including vitamin E, which is preferred), sterically hindered phenols (BHT), those materials which are readily oxidized, such as sulfites, ascorbic acid, ferrous sulfate, and stannous chloride, and those which can absorb oxygen (e.g., by chemisorption), such as porphyrins.

If liquid antioxidants such as vitamin E are used, such liquids could be immobilized on the inside surface of the inserter. Blending the vitamin E with the resin used to produce the inserter would be an alternative means of making it available to protect against $O_2$.

According to still another embodiment, an oxygen absorber can be incorporated into the inserter material. Suitable thermoplastic resins include olefins, polyesters and polyamides. Suitable oxygen absorbing agents include metallic type agents having a metal such as iron as a main component and organic type agents having an organic compound such as ascorbic acid as a main component. Those and other suitable thermoplastic resins and oxygen absorbers are disclosed in European Patent Application EP 0 720 821 A2, the disclosure of which is hereby incorporated by reference.

According to another embodiment of the invention, the pad having a reduced $O_2$ level can also comprise an antioxidant which will combine with or scavenge any residual oxygen molecules not removed from the tampon pad or otherwise replaced by other gases. Additionally, an antioxidant will combine with or scavenge any $O_2$ molecules present during storage or which diffuse into the tampon during storage or which may infiltrate into a pad during its insertion into the body. Suitable antioxidants include those having a conjugated double bond, sterically hindered phenols, porphyrins, ascorbic acid, vitamin E, ferrous sulfate, stannous chloride or any of a variety of well known safe antioxidants. Further, because $CO_2$ has an effect in promoting the production of toxic shock syndrome exotoxin the pads of the invention may further comprise $CO_2$ scavengers such as water to scavenge any $CO_2$ which is present or infiltrates into the pad.

As a further aspect of the present invention, bactericides may be incorporated into the pads with those bactericides which are specific for *Staphylococcus aureus* being preferred. Means such as buffer agents may also be incorporated into the pads so as to maintain the pH of the fluids absorbed in the tampon in the range of about 2.5 to 5.5.

Various methods well within the skill in the art may be used to reduce the level of $O_2$ in the tampon of the invention. According to such methods, the absorptive pads may be produced and packaged (i.e., sealed in the inserter) under reduced pressure so as to minimize the level of $O_2$ and $CO_2$ present in the interstices of the pad. Alternatively, or in the combination with producing and packaging the products under reduced pressure, atmospheric air containing $O_2$ and $CO_2$ may be replaced with a biocompatible gas such as nitrogen ($N_2$), neon, helium, argon, a fluorinated hydrocarbon, or another suitable biocompatible gas that has a vapor pressure of greater than 1 atmosphere at 0° C. and which does not promote the production of toxic shock syndrome exotoxin. The tampon itself (while inside the inserter) or the tampon/inserter combination may be sealed in a wrap made from plastic, paraffin or other material which prevents $O_2$ and $CO_2$ infiltration. The wrap preferably has a permeation coefficient for nitrogen of less than about $3\times10^{-9}$ ($cm^3$ mm)/(sec $cm^2$ cm Hg) and a permeation coefficient for oxygen less than about $1.5\times10^{-9}$ ($cm^3$ mm)/(sec $cm^2$ cm Hg). The wrap helps maintain biocompatible gas overpressure within the tampon and inserter. The tampon of the present invention may also comprise an overwrap such as the overwrap disclosed in Baier, et al., U.S. Pat. No. 3,902,493.

According to still another method, production and packaging of the tampons of the invention may be carried out under conditions wherein atmospheric air is replaced with a biocompatible gas such as nitrogen, neon, argon, helium, a fluorinated hydrocarbon, or another suitable gas having a vapor pressure of greater than 1 atmosphere at 0° C. The tampon is preferably packaged or sealed in the inserter in the presence of biocompatible gases at an elevated positive pressure such that $O_2$ and $CO_2$ infiltration into the product is minimized.

According to still another embodiment of the invention, $O_2$ scavengers can be incorporated into the tampons having reduced $O_2$ and $CO_2$ levels during the manufacturing process. The scavengers will act to scavenge residual oxygen molecules not removed from the pads or otherwise replaced by other gases. Suitable oxygen scavenging materials include ascorbic acid, vitamin E, ferrous sulfate, stannous chloride or any of a variety of well known, safe oxygen scavengers. Such scavengers may be incorporated into the absorptive pads of the invention at levels ranging from about 10 mg to about 500 mg. Further, the oxygen scavengers can be added to the absorptive pad during the manufacturing process according to well known methods such as by applying solutions of the scavengers to the pads and drying the pads. Alternatively, the scavengers can be added in solutions of water or tocopherol (Vitamin E) which act as lubricants. Where the oxygen scavengers are added to the pads the scavenging effect can occur both during storage of the pad as well as after insertion into the body. Alternatively, the oxygen scavengers can be incorporated to the packaging or inserter to inhibit oxygen migration into the product during storage.

Because $CO_2$ may stimulate toxic shock exotoxin production, $CO_2$ scavengers can also be added to the absorptive pad or packaging to scavenge $CO_2$. According to one embodiment of the invention, water itself is added to the pad as a scavenger for $CO_2$ which can then dissolve into the water forming carbonic acid. An effective amount of $CO_2$ scavengers may be incorporated into the inserter.

It is anticipated that numerous variations and modifications of the embodiments described above win occur to those of ordinary skill in the art when apprised of the teachings of the present specification. Accordingly, only such limitations as appear in the appended claims should be placed thereon.

What is claimed is:

1. A combination catamenial tampon and inserter comprising a catamenial tampon characterized by having an $O_2$ concentration sufficiently reduced so as to reduce the introduction of oxygen into a vagina during insertion of said tampon, and an inserter enclosing the tampon and reducing contamination of the tampon with environmental $O_2$ during storage, wherein the pressure inside of the inserter during storage is less than atmospheric pressure.

2. The combination tampon and inserter of claim 1 wherein said tampon comprises materials selected from the group consisting of cotton fibers and rayon fibers.

3. The combination tampon and inserter of claim 1 wherein the inserter comprises a sealed cylinder containing the tampon and a means for discharging the tampon at one end of the cylinder, wherein during insertion of the tampon into a vagina the discharge means is depressed into the cylinder rupturing the end of the cylinder distal to the discharge means and introducing the tampon into the vagina.

4. The combination tampon and inserter of claim 1 wherein the tampon comprises an antioxidant.

5. The combination tampon and inserter of claim 4 wherein the antioxidant is selected from the group consisting of compounds comprising conjugated double bonds, porphyrins, sterically hindered phenols, ascorbic acid, vitamin E, ferrous sulfate, and stannous chloride.

6. The combination tampon and inserter of claim 1 wherein the tampon is characterized by having a $CO_2$ level sufficiently reduced so as to reduce introduction of $CO_2$ into the vaginal cavity by the tampon.

7. A combination catamenial tampon and inserter comprising a catamenial tampon characterized by having an $O_2$ concentration sufficiently reduced so as to reduce the introduction of oxygen into a vagina during insertion of said tampon, and an inserter enclosing the tampon and reducing contamination of the tampon with environmental $O_2$ during storage, wherein the inserter enclosing the tampon contains a suitable biocompatible gas having a vapor pressure of greater than 1 atmosphere at 0° C., wherein said gas does not promote production of toxic shock syndrome exotoxin.

8. The combination tampon and inserter of claim 7 wherein the suitable biocompatible gas is selected from the group consisting of $N_2$, neon, argon, helium, and fluorinated hydrocarbons having a vapor pressure greater than 1 atmosphere at 0° C.

9. The combination tampon and inserter of claim 7 wherein suitable materials for forming the inserter are polymers that have a permeation coefficient for $N_2$ less than $3\times10^{-9}$ ($cm^3$ mm)/(sec $cm^2$ cm Hg) and a permeation coefficient for $O_2$ less than $1.5\times10^{-9}$ ($cm^3$ mm)/(sec $cm^2$ cm Hg).

10. The combination tampon and inserter of claim 7 wherein the inserter comprises a plunger and a bellows disposed around the plunger to reduce the replacement of the biocompatible gas by $O_2$ during storage and insertion.

11. The combination tampon and inserter of claim 7 wherein the inserter comprises a plunger and a cylinder for receiving the plunger during tampon insertion, wherein a seal is formed between the plunger and an interior surface of the cylinder to reduce the replacement of the biocompatible gas by $O_2$ during storage and insertion.

12. The combination tampon and inserter of claim 7 wherein said tampon comprises materials selected from the group consisting of cotton fibers and rayon fibers.

13. The combination tampon and inserter of claim 7 wherein the inserter comprises a sealed cylinder containing the tampon and a means for discharging the tampon at one end of the cylinder, wherein during insertion of the tampon into a vagina the discharge means is depressed into the cylinder rupturing the end of the cylinder distal to the discharge means and introducing the tampon into the vagina.

14. The combination tampon and inserter of claim 7 wherein the tampon comprises an antioxidant.

15. The combination tampon and inserter of claim 14 wherein the antioxidant is selected from the group consisting of compounds comprising conjugated double bonds, porphyrins, sterically hindered phenols, ascorbic acid, vitamin E, ferrous sulfate, and stannous chloride.

16. The combination tampon and inserter of claim 7 wherein the tampon is characterized by having a $CO_2$ level sufficiently reduced so as to reduce introduction of $CO_2$ into the vaginal cavity by the tampon.

17. A combination catamenial tampon and inserter comprising a catamenial tampon characterized by having an $O_2$ concentration sufficiently reduced so as to reduce the introduction of oxygen into a vagina during insertion of said tampon, and an inserter enclosing the tampon and reducing contamination of the tampon with environmental $O_2$ during storage wherein an amount of antioxidant effective to reduce the production of toxic shock syndrome exotoxin is incorporated into the inserter.

18. The combination tampon and inserter of claim 17 wherein the antioxidant is selected from the group consisting of compounds comprising conjugated double bonds, porphyrins, sterically hindered phenols, ascorbic acid, vitamin E, ferrous sulfate, and stannous chloride.

19. A combination catamenial tampon and inserter comprising a catamenial tampon characterized by having an $O_2$ concentration sufficiently reduced so as to reduce the introduction of oxygen into a vagina during insertion of said tampon, and an inserter enclosing the tampon and reducing contamination of the tampon with environmental $O_2$ during storage wherein an amount of $CO_2$ scavenger effective to reduce the production of toxic shock syndrome exotoxin is incorporated into the tampon.

20. A combination catamenial tampon, inserter, and bag, the combination comprising a catamenial tampon characterized by having an $O_2$ concentration sufficiently reduced so as to reduce the introduction of oxygen into a vagina during insertion of said tampon, an inserter enclosing the tampon and reducing contamination of the tampon with environmental $O_2$ during storage, and a gas impervious laminate film bag having a permeation coefficient for nitrogen of less than about $3\times10^{-9}$ ($cm^3$ mm)/(sec $cm^2$ cm Hg) and a permeation coefficient for oxygen less than about $1.5\times10^{-9}$ ($cm^3$ mm)/(sec $cm^2$ cm Hg), the tampon and the inserter being disposed in the bag during storage, and the pressure inside of the bag during storage being less than atmospheric pressure.

21. A method of producing a combination tampon and inserter comprising a catamenial tampon characterized by having an $O_2$ concentration sufficiently reduced so as to reduce the introduction of oxygen into a vagina during insertion of said tampon, and an inserter enclosing the tampon and reducing contamination of the tampon with environmental $O_2$ during storage comprising the steps of (1) producing a catamenial tampon, (2) replacing at least some of the $O_2$ present in the tampon with a biocompatible gas which does not promote production of toxic shock syndrome exotoxin, (3) providing an inserter, and (4) sealing the tampon with said inserter enclosing the tampon.

22. A method of producing a combination tampon and inserter comprising a catamenial tampon characterized by having an $O_2$ concentration sufficiently reduced as to be effective in reducing the production of toxic shock syndrome exotoxin during internal use of said tampon, and an inserter enclosing the tampon and reducing contamination of the tampon with environmental $O_2$ during storage comprising the steps of (1) producing a catamenial tampon under substantially $O_2$-free conditions, (2) providing an inserter, and (3) sealing the tampon with said inserter enclosing the tampon.

23. The method of claim 22 wherein the catamenial tampon is produced in the presence of a biocompatible gas which does not promote production of toxic shock syndrome exotoxin.

24. A combination catamenial tampon and inserter characterized by having an $O_2$ level sufficiently reduced as to be effective in reducing the production of toxic shock syndrome exotoxin during internal use of said tampon, said tampon containing a biocompatible gas, an antioxidant, a $CO_2$ scavenger, and said inserter containing a biocompatible gas at an elevated positive pressure, and an antioxidant.

25. A method of producing a combination tampon and inserter comprising a catamenial tampon characterized by having an $O_2$ concentration sufficiently reduced so as to reduce the introduction of oxygen into a vagina during insertion of said tampon, and an inserter enclosing the tampon and reducing contamination of the tampon with environmental $O_2$ during storage comprising the steps of (1) producing a catamenial tampon under reduced pressure, (2) providing an inserter, and (3) sealing the tampon with said inserter enclosing the tampon, wherein the pressure inside of the inserter after sealing is less than atmospheric pressure.

26. A combination catamenial tampon, inserter, and bag, the combination comprising a catamenial tampon characterized by having an $O_2$ concentration sufficiently reduced so as to reduce the introduction of oxygen into a vagina during insertion of said tampon, an inserter enclosing the tampon and reducing contamination of the tampon with environmental $O_2$ during storage, and a gas impervious laminate film bag having a permeation coefficient for nitrogen of less than about $3\times10^{-9}$ ($cm^3$ mm)/(sec $cm^2$ cm Hg) and a permeation coefficient for oxygen less than about $1.5\times10^{-9}$ ($cm^3$ mm)/(sec $cm^2$ cm Hg), wherein the tampon and the inserter are disposed in the bag during storage, the bag enclosing the tampon and inserter contains a suitable biocompatible gas having a vapor pressure of greater than 1 atmosphere at 0° C., and said gas does not promote production of toxic shock syndrome exotoxin.

* * * * *

UNITED STATES PATENT AND TRADEMARK OFFICE
CERTIFICATE OF CORRECTION

PATENT NO. : 5,817,047
DATED : October 6, 1998
INVENTOR(S) : Osborn, III et al.

It is certified that error appears in the above-identified patent and that said Letters Patent is hereby corrected as shown below:

At Column 3, line 66, delete "or" and insert --for-- therefor.

At Column 6, line 42, delete "preferred)" and insert --(preferred)-- therefor.

At Column 8, line 63, delete "win" and insert --will-- therefor.

Signed and Sealed this

Twenty-third Day of March, 1999

*Attest:*

Q. TODD DICKINSON

*Attesting Officer*     *Acting Commissioner of Patents and Trademarks*